United States Patent
Jarc

(10) Patent No.: US 12,023,122 B2
(45) Date of Patent: *Jul. 2, 2024

(54) UNGROUNDED MASTER CONTROL DEVICES AND METHODS OF USE

(71) Applicant: Intuitive Surgical Operations, Inc., Sunnyvale, CA (US)

(72) Inventor: Anthony M. Jarc, Cupertino, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 208 days.

This patent is subject to a terminal disclaimer.

(21) Appl. No.: 17/833,667

(22) Filed: Jun. 6, 2022

(65) Prior Publication Data

US 2022/0313379 A1     Oct. 6, 2022

Related U.S. Application Data

(62) Division of application No. 15/753,052, filed as application No. PCT/US2016/047212 on Aug. 16, 2016, now Pat. No. 11,351,001.

(Continued)

(51) Int. Cl.
*A61B 34/37* (2016.01)
*A61B 1/04* (2006.01)
(Continued)

(52) U.S. Cl.
CPC ............... *A61B 34/37* (2016.02); *A61B 1/04* (2013.01); *A61B 5/11* (2013.01); *A61B 34/35* (2016.02);
(Continued)

(58) Field of Classification Search
CPC ....... A61B 1/04; A61B 5/11; A61B 2034/742; A61B 2017/00438; A61B 34/37; A61B 34/35; A61B 34/74; G06F 3/0346
See application file for complete search history.

(56) References Cited

U.S. PATENT DOCUMENTS 3,350,956 A    11/1967  Barton et al.
5,176,696 A     1/1993  Saunders
(Continued)

FOREIGN PATENT DOCUMENTS

EP    2289454 A2    3/2011
EP    3015081 A1    5/2016
(Continued)

OTHER PUBLICATIONS

International Preliminary Report on Patentability for Application No. PCT/US2016/047212, mailed on Mar. 1, 2018, 8 pages (ISRG07680/PCT).

(Continued)

*Primary Examiner* — Alyssa M Alter
*Assistant Examiner* — Jessandra F Hough
(74) *Attorney, Agent, or Firm* — IP Spring

(57) ABSTRACT

A mechanically ungrounded master control device comprises a rigid chassis for engagement with one or more fingers of a user's hand and at least one pivotable finger engagement device for controlling movement of a tool end effector. The control device also includes at least one sensor for detecting a position and orientation of the rigid chassis in a surgical environment and a switch coupled to the rigid chassis and manipulatable by a finger of the user's hand while another finger of the user's hand is engaged with the at least one pivotable finger engagement device.

22 Claims, 5 Drawing Sheets

Related U.S. Application Data

(60) Provisional application No. 62/206,025, filed on Aug. 17, 2015.

(51) Int. Cl.
  *A61B 5/11* (2006.01)
  *A61B 17/00* (2006.01)
  *A61B 34/00* (2016.01)
  *A61B 34/35* (2016.01)
  *G06F 3/0346* (2013.01)

(52) U.S. Cl.
  CPC .... *A61B 34/74* (2016.02); *A61B 2017/00438* (2013.01); *A61B 2034/742* (2016.02); *G06F 3/0346* (2013.01)

(56) References Cited

U.S. PATENT DOCUMENTS

| | | |
|---|---|---|
| 5,876,325 A | 3/1999 | Mizuno et al. |
| 5,976,121 A | 11/1999 | Matern et al. |
| 8,016,818 B2 | 9/2011 | Ellis et al. |
| 8,521,331 B2 | 8/2013 | Itkowitz |
| 8,638,057 B2 | 1/2014 | Goldberg et al. |
| 11,351,001 B2 | 6/2022 | Jarc |
| 2002/0040217 A1* | 4/2002 | Jinno ................. B25J 3/04 606/1 |
| 2006/0178559 A1 | 8/2006 | Kumar et al. |
| 2008/0058836 A1 | 3/2008 | Moll et al. |
| 2008/0262538 A1 | 10/2008 | Danitz et al. |
| 2009/0030428 A1 | 1/2009 | Omori et al. |
| 2010/0069940 A1 | 3/2010 | Miller et al. |
| 2010/0228156 A1 | 9/2010 | Valero-Cuevas et al. |
| 2011/0118753 A1 | 5/2011 | Itkowitz et al. |
| 2012/0041595 A1 | 2/2012 | Greeley et al. |
| 2013/0035697 A1 | 2/2013 | Ogawa et al. |
| 2013/0207890 A1 | 8/2013 | Young |
| 2014/0018960 A1 | 1/2014 | Itkowitz |
| 2014/0160015 A1 | 6/2014 | Ogawa et al. |
| 2014/0165770 A1 | 6/2014 | Abri et al. |
| 2014/0276646 A1 | 9/2014 | Wong et al. |
| 2015/0073340 A1 | 3/2015 | Pacheco et al. |
| 2015/0290814 A1 | 10/2015 | Schiele et al. |
| 2016/0202134 A1 | 7/2016 | Malackowski et al. |
| 2016/0216167 A1 | 7/2016 | Blumenkranz et al. |
| 2017/0095298 A1 | 4/2017 | Vakharia et al. |
| 2017/0296280 A1 | 10/2017 | Ogawa et al. |

FOREIGN PATENT DOCUMENTS

| | | |
|---|---|---|
| EP | 3245975 A1 | 11/2017 |
| JP | 2006321027 A | 11/2006 |
| WO | WO-2008133956 A2 | 11/2008 |
| WO | WO-2012127404 A2 | 9/2012 |
| WO | WO-2013018933 A1 | 2/2013 |
| WO | WO-2016154173 A1 | 9/2016 |
| WO | WO-2016201544 A1 | 12/2016 |
| WO | WO-2017031132 A1 | 2/2017 |
| WO | WO-2019099504 A1 | 5/2019 |
| WO | WO-2019099584 A1 | 5/2019 |
| WO | WO-2019217882 A1 | 11/2019 |

OTHER PUBLICATIONS

International Search Report and Written Opinion for Application No. PCT/US2016/047212, mailed on Nov. 17, 2016, 11 pages (ISRG07680/PCT).

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

UNGROUNDED MASTER CONTROL DEVICES AND METHODS OF USE

CROSS-REFERENCE TO RELATED APPLICATIONS

This patent application is a divisional of U.S. patent application Ser. No. 15/753,052, filed on Feb. 15, 2018, which is a U.S. National Stage Filing under 35 U.S.C. § 371 of International Patent Application No. PCT/US2016/047212, filed on Aug. 16, 2016, which claims priority to and the benefit of the filing date of U.S. Provisional Patent Application No. 62/206,025, entitled "UNGROUNDED MASTER CONTROL DEVICES AND METHODS OF USE," filed Aug. 17, 2015, the contents of each of which are incorporated by reference herein in their entirety.

FIELD

The present disclosure is directed to a computer-assisted, minimally invasive teleoperated surgical systems, and more particularly to surgeon interfaces for minimally invasive teleoperated surgical systems.

BACKGROUND

Minimally invasive medical techniques are intended to reduce the amount of tissue that is damaged during invasive medical procedures, thereby reducing patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments. Imaging instruments provide a user with a field of view within the patient anatomy. Some minimally invasive medical tools and imaging instruments may be teleoperated or otherwise computer-assisted. A teleoperated medical system may include a dedicated surgeon's console which provides a three-dimensional stereo viewer and one or more master manipulator control devices for operating the minimally invasive medical tools. For purposes of training users of teleoperated medical systems, control devices are needed to allow a proctor to provide instruction to a surgical trainee working at the surgeon's console. Control devices are also needed to allow a surgeon to move within an environment while performing a teleoperated procedure. In some situations, it may be beneficial to operate such control devices without being bound to a stationary surgeon's console.

SUMMARY

The embodiments of the invention are summarized by the claims that follow below.

In one embodiment, a mechanically ungrounded master control device comprises a rigid chassis for engagement with one or more fingers of a user's hand and at least one pivotable finger engagement device for controlling movement of a tool end effector. The control device also includes at least one sensor for detecting a position and orientation of the rigid chassis in a surgical environment and a switch coupled to the rigid chassis and manipulatable by a finger of the user's hand while another finger of the user's hand is engaged with the at least one pivotable finger engagement device.

In another embodiment, a teleoperated medical system comprises a mechanically ungrounded master control device including a rigid chassis for engagement with one or more fingers of a user's hand and at least one pivotable finger engagement device for controlling movement of a virtual tool end effector. The a mechanically ungrounded master control device also includes at least one sensor for detecting a position and orientation of the rigid chassis in a surgical environment and a switch coupled to the rigid chassis and manipulatable by a finger of the user's hand while another finger of the user's hand is engaged with the at least one pivotable finger engagement device. The teleoperated medical system also comprises a surgeon's console including a mechanically grounded master control device for controlling a surgical tool and a display for displaying the virtual tool end effector and the surgical tool and a manipulator for manipulating the surgical tool in response to movement of the mechanically grounded master control device.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1:
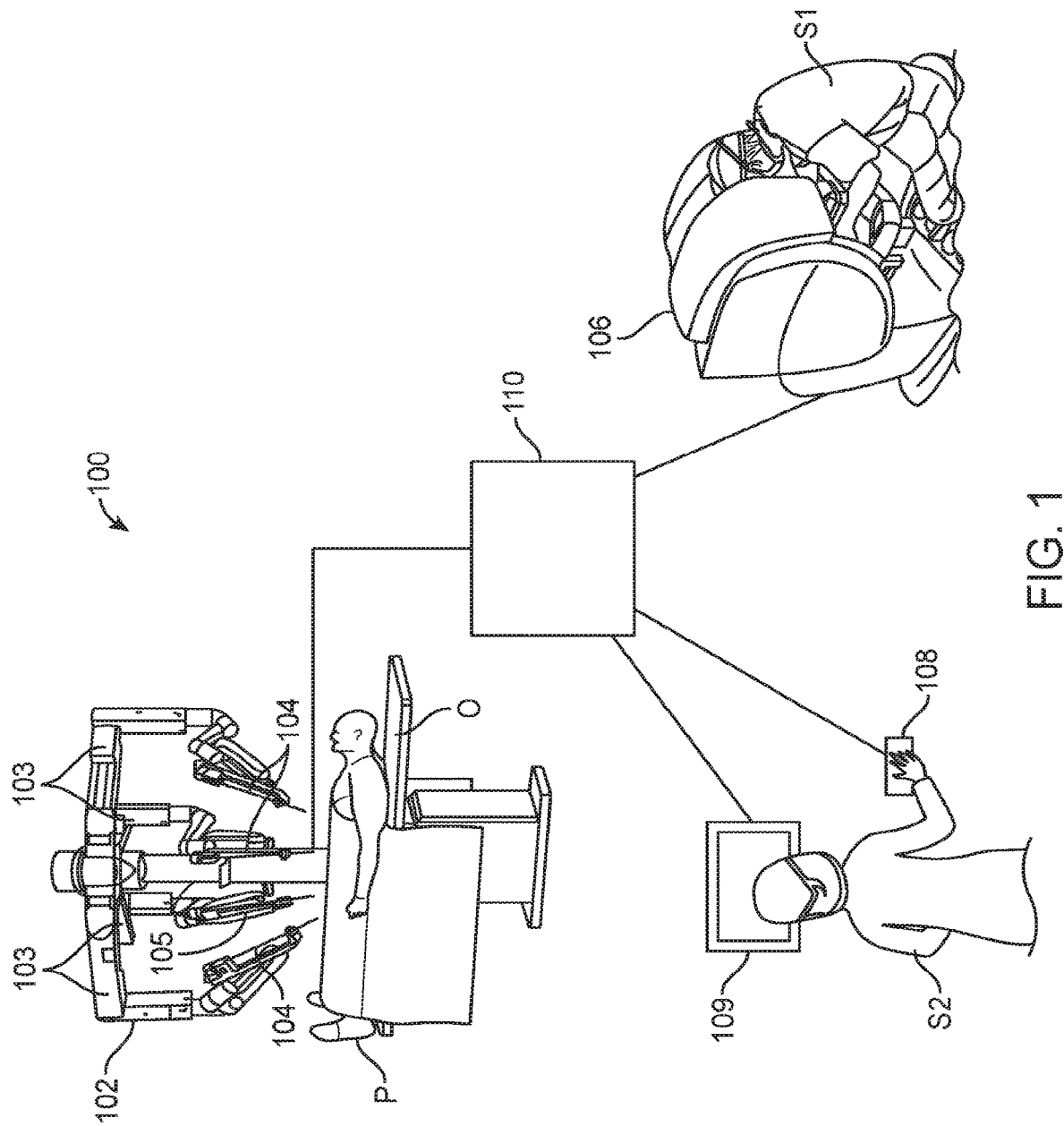
FIG. 1 is a diagrammatic view of a teleoperated medical system.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw around the Cartesian X, Y, and Z axes). As used herein, the term "pose" refers to the position of an object or a portion of an object in at least one degree of translational freedom and to the orientation of that object or portion of the object in at least one degree of rotational freedom (up to six total degrees of freedom).

As used herein, mechanically ungrounded master control device means a master tool control device that is unconstrained with respect to possible position and orientation motion in a large working environment and is kinematically separated from a surgeon's console. A mechanically ungrounded master control device may be in tethered or untethered connection with one or more associated control processors, data sources, sensors, and power supplies.

Aspects of this invention augment the control capability of a computer-assisted teleoperated medical system through the use of one or more mechanically ungrounded master control devices (e.g., one, two, three, or more) for providing instruction, supervision, proctoring, and other feedback to a user of the system. Mechanically ungrounded master control devices may provide control of one or more of the operational surgical tools in the surgical environment or proxy surgical tools in a virtual environment. The da Vinci® minimally invasive teleoperated medical system commercialized by Intuitive Surgical, Inc. of Sunnyvale, Calif., is one example of a medical device system that may incorporate one or more of these mechanically ungrounded master control devices.

FIG. 1 is a diagrammatic view of a minimally invasive teleoperated surgical system 100 including a mechanically ungrounded master control device. Further information regarding minimally invasive surgical systems may be found for example in U.S. Pat. No. 6,714,839 (issued on Mar. 30, 2004, disclosing "Master Having Redundant Degrees of Freedom;" U.S. Pat. No. 9,060,678 (issued Jun. 23, 2015, disclosing "Minimally Invasive Surgical System"); and U.S. Pat. No. 6,331,181 (issued on Dec. 18, 2001, disclosing "Surgical Robotic Tools, Data Architecture, And Use"), all of which are incorporated herein by reference.

As shown in FIG. 1, the teleoperated medical system 100 generally includes a teleoperated assembly 102 mounted to or near an operating table O on which a patient P is positioned. The teleoperated assembly 102 may be referred to as a patient side cart and includes a plurality of manipulator arms 103. One or more medical instrument systems 104 and an endoscopic imaging system 105 are operably coupled to the teleoperated assembly 102. An operator input system 106 allows a surgeon or other type of clinician S1 to view images of or representing the surgical site and to control the operation of the manipulator arms 103, the medical instrument systems 104, and/or the endoscopic imaging system 105.

The operator input system 106 may be located at a surgeon's console, which is usually located in the same room as operating table O. It should be understood, however, that the surgeon S1 can be located in a different room or a completely different building from the patient P. Operator input system 106 generally includes one or more mechanically grounded control device(s) for controlling the manipulators 103, the medical instrument system 104, and the imaging system 105. The control device(s) may include one or more of any number of a variety of coupled input devices, such as kinematically linked hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperated assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move in all six Cartesian degrees of freedom, and which may also include an actuatable handle for actuating instruments (for example, for closing grasping jaws, applying an electrical potential to an electrode, delivering a medicinal treatment, and the like). Such a grip function is an additional mechanical degree of freedom (i.e., a grip DOF).

The teleoperated medical system 100 also includes one or more mechanically ungrounded master control devices 108, as will be described below in detail for various embodiments of this disclosure, for use by a user S2 who may be a surgeon controlling the movement of instruments 104 or imaging system 105 or a proctor providing supervision and/or instruction for surgeon S1. Each manipulator arm 103 and the teleoperated slave surgical instrument controlled by that manipulator can be coupled to and decoupled from master control devices on surgeon's console 106, and in addition they may be coupled to and decoupled from mechanically ungrounded master control devices 108. The user S2 may visualize a surgical environment within the patient P and the real or virtual instruments controlled by the ungrounded master control device 108 on a display system 109. Various embodiments of an ungrounded master control device are disclosed in U.S. Pat. No. 8,521,331 (issued on Aug. 27, 2013, disclosing "Patient-side Surgeon Interface For a Minimally Invasive, Teleoperated Surgical Instrument"), which is incorporated herein by reference in its entirety.

The teleoperated medical system 100 also includes a control system 110. The control system 110 includes at least one memory and at least one processor (not shown), and typically a plurality of processors, for effecting control between the medical instrument system 104, the operator input system 106, the mechanically ungrounded master control device 108, and the display system 109. The control system 110 also includes programmed instructions (e.g., a computer-readable medium storing the instructions) to implement some or all of the methods described in accordance with aspects disclosed herein. While control system 110 is shown as a single block in the simplified schematic of FIG. 1, the system may include two or more data processing circuits with one portion of the processing optionally being performed on or adjacent the teleoperated assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperated systems described herein. In one embodiment, control system 110 supports one or more wireless communication protocols such as Bluetooth, IrDA, HomeRF, IEEE 802.11, DECT, and Wireless Telemetry.

The teleoperated medical system 100 may further include optional operation and support systems (not shown) such as illumination systems, steering control systems, irrigation systems, and/or suction systems. In alternative embodiments, the teleoperated system may include more than one teleoperated assembly and/or more than one operator input system. The exact number of manipulator arms will depend on the surgical procedure and the space constraints within the operating room, among other factors. The operator input systems may be collocated or they may be positioned in separate locations. Multiple operator input systems allow more than one operator to control one or more manipulator assemblies in various combinations.

In one aspect, the mechanically ungrounded master control device 108 is used to control any one of a plurality of proxy visuals that can be used by a surgeon to proctor another surgeon. For example, when surgeon S1 (FIG. 1) is being proctored by surgeon S2, surgeon S2 uses control device 108 to control a proxy visual of a surgical instrument, while surgeon S1 uses the master tool control devices of the surgeon's console 106 to control a teleoperated slave surgical tool 104.

Alternatively, surgeon S2 can telestrate (i.e., draw a freehand sketch over a moving or still video image), or can control a virtual hand or other pointer in the display. Also, surgeon S2 can demonstrate how to manipulate the master tool grip on the surgeon's console 106 by manipulating a virtual image of master tool grip that is presented in the display. These examples of proxy visuals are illustrative only and are not intended to be limiting.

To facilitate proctoring, a proxy visual module (not shown) of the controller 110 is processed as part of a vision processing subsystem in one aspect. In this aspect, the executing module receives position and orientation information, switch states, presence states, grip state, variable slider state, or other information from the control device 108 and renders stereo images, which are composited with the endoscopic camera images in real time and displayed on any combination of surgeon console 106, display system 109, or any other display systems in the surgical environment.

In one aspect, the display system 109 and/or the display on the surgeon's console 106 displays an image 200 of the surgical environment within the patient P along with a proxy visual, which in this embodiment is a virtual (i.e., ghost) instrument 202 controlled by control device 108. The image 200 of the surgical environment also displays teleoperated slave surgical instrument 204 (e.g., tool 104) controlled by one of the master tool manipulators of surgeon's console 106. Surgeon S2 sees both instruments 202 and 204 in display device 109, while surgeon S1 sees both instrument 202 and 204 in the stereoscopic display in surgeon's console 106. The use of virtual (ghost) instrument 202 as a proxy visual is illustrative only and is not intended to be limiting to this particular image. In view of this disclosure, other images can be used for the proxy visual, which facilitate differentiation between the image representing the proxy visual and the image of the actual end effector of the teleoperated slave surgical instrument.

Virtual instrument 202 appears similar to actual instrument 204, except virtual instrument 202 is displayed in a way that clearly distinguishes virtual ghost instrument 202 from actual instrument 204 (e.g., a transparent or translucent ghost-like image, a distinctly colored image, a smaller sized instrument relative to the actual instruments, an obvious artificial rendering, etc.). The control and operation of virtual instrument 202 is the same as that described above for an actual teleoperated surgical instrument. Thus, surgeon S2 can manipulate virtual ghost instrument 202 using control device 108 to demonstrate the proper use of teleoperated slave surgical instrument 204. Surgeon S1 can mimic the motion of virtual ghost instrument 202 with instrument 204.

Virtual instruments are described more completely in commonly assigned U.S. patent application Ser. No. 14/629, 685 (filed Feb. 24, 2015, disclosing "Method and Apparatus for Hand Gesture Control in a Minimally Invasive Surgical System.") and U.S. Patent Application No. U.S. Ser. No. 12/415,332 (filed Mar. 31, 2009; disclosing "Synthetic Representation of a Surgical Instrument"), which are incorporated herein by reference in their entirety. See also, U.S. patent application Ser. No. 12/485,503 (filed Jun. 16, 2009, disclosing "Virtural Measurement Tool for Minimally Invasive Surgery"); U.S. patent application Ser. No. 12/485,545 (filed Jun. 16, 2009, disclosing "Virtual Measurement Tool for Minimally Invasive Surgery"); U.S. Patent Application Publication No. US 2009/0036902 A1 (filed Aug. 11, 2008; disclosing "Interactive User Interfaces for Robotic Minimally Invasive Surgical Systems"); U.S. Patent Application Publication No. US 2007/0167702 A1 (filed Dec. 30, 2005; disclosing "Medical Robotic System Providing Three-Dimensional Telestration"); U.S. Patent Application Publication No. US 2007/0156017 A1 (filed Dec. 30, 2005; disclosing "Stereo Telestration for Robotic Surgery"); and U.S. Patent Application Publication No. US 2010/0164950 A1 (filed May 13, 2009; disclosing "Efficient 3-D Telestration for Local Robotic Proctoring"), each of which is incorporated herein by reference in its entirety.

Figure 2:
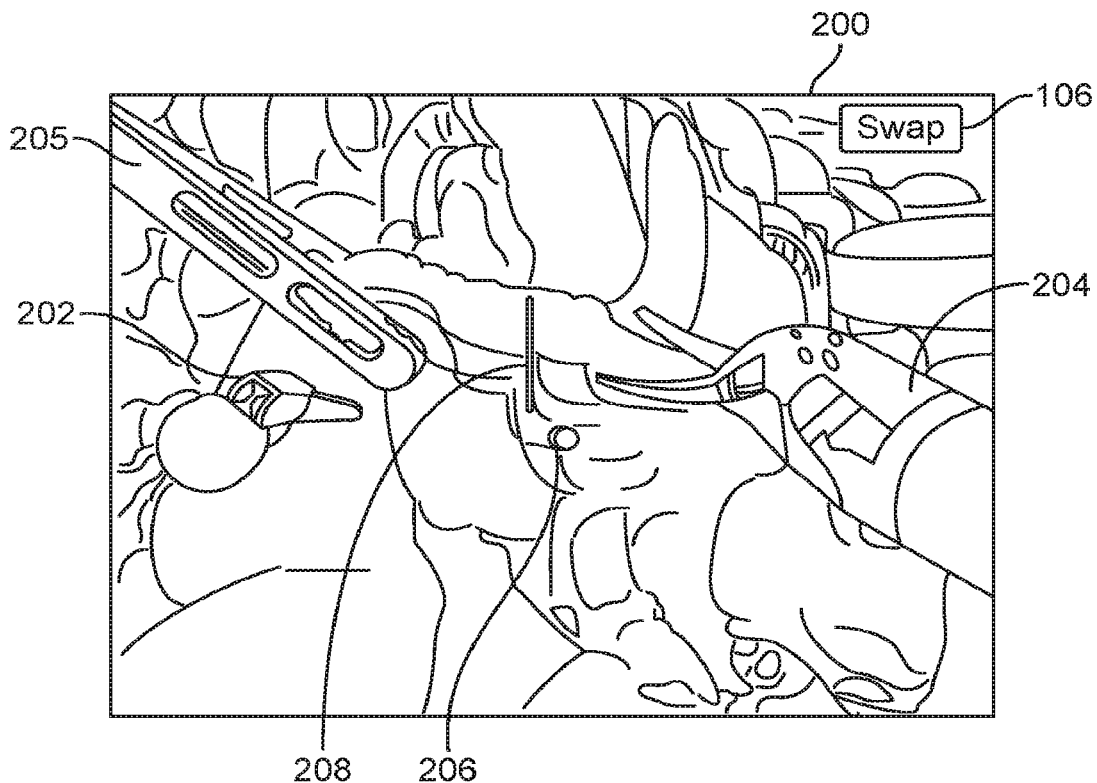
FIGS. 2 and 3 are images presented on a display device, including proxy visuals.

In another aspect, the proxy visual includes a virtual telestration device 206. Telestration device 206 may be controlled by the control device 106 or by another mechanically ungrounded master control device under the control of user S2 or another proctor user. To telestrate with virtual telestration device 206, user S2 places the thumb and forefinger together as if grasping an imaginary pen or pencil and then moves the right hand with the thumb and forefinger in this position to telestrate in the displayed image. As shown in FIG. 2, by using image 200, user S2 has so positioned the thumb and forefinger and made mark 208 to illustrate where the tissue is to be cut using surgical instrument 204.

In another aspect, the image 200 includes an interface button 209 overlaid upon the actual instrument image, the virtual instrument image, or the image of the patient anatomy. The virtual button 209 may be selected by proxy visual instrument (e.g., the virtual instrument 202, virtual hand 210, or telestration device 206) to change some configuration of the proxy visual instrument. For example, selecting the button 209 may cause the image of the proxy visual instrument to swap forms. For example, if the virtual instrument selects the button 209, the virtual instrument may be swapped for an image of a virtual hand. Alternatively, the virtual button may operate any of the functions describe for the switches (e.g., switch 324, 430, 510) of the embodiments described below.

Figure 3:
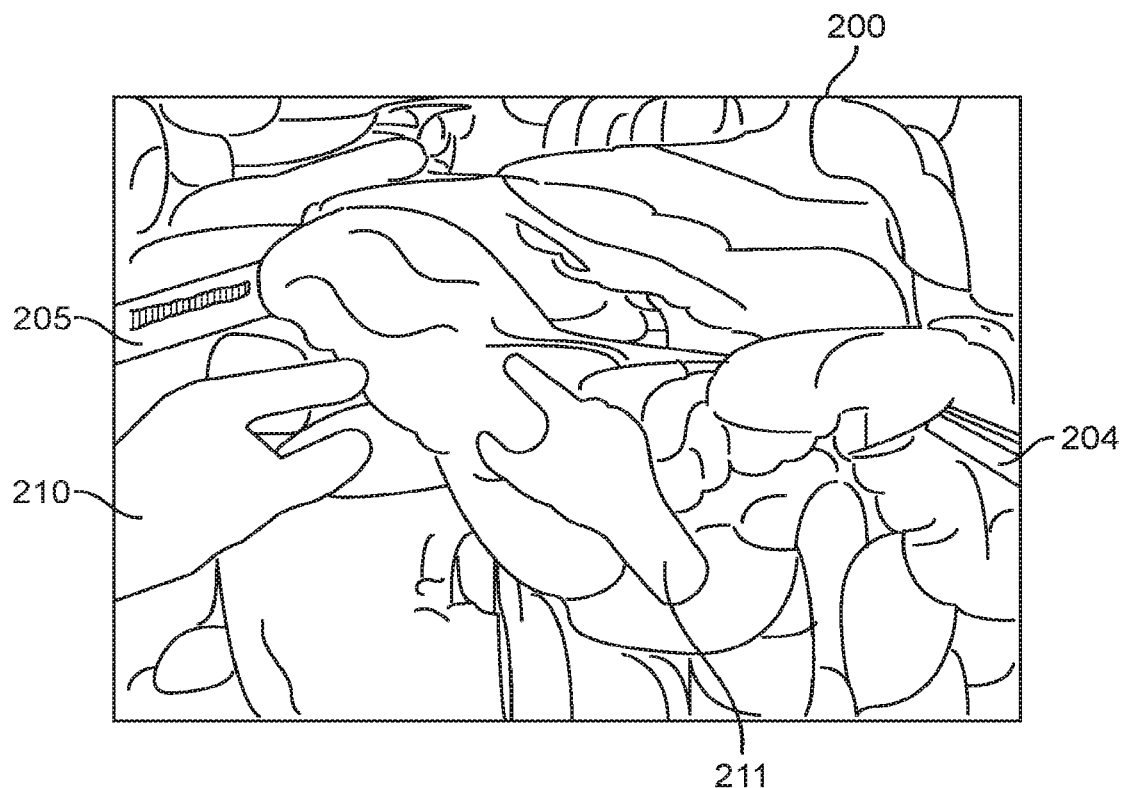

In another aspect, as shown in FIG. 3, the proxy visual is a pair of virtual hands 210, 211 controlled by control device 108 and a second control device controlled by the user S2, which is not visible in FIG. 1. Teleoperated slave surgical instruments 204, 205 are controlled by the master tool manipulators of surgeon's console 106. Surgeon S2 sees video image 200 in display device 109, and surgeon S1 also sees video image 200 in the stereoscopic display in surgeon's console 106.

Figure 4:
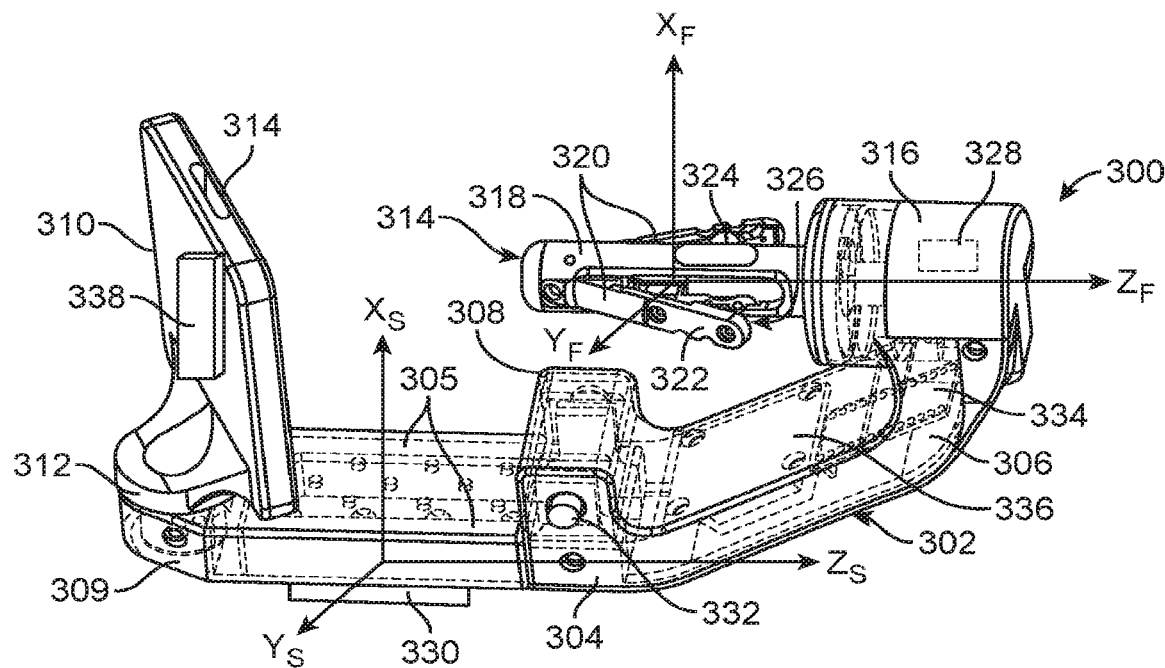
FIG. 4 is a perspective view of a mechanically ungrounded master control device according to one embodiment.
Figure 5:
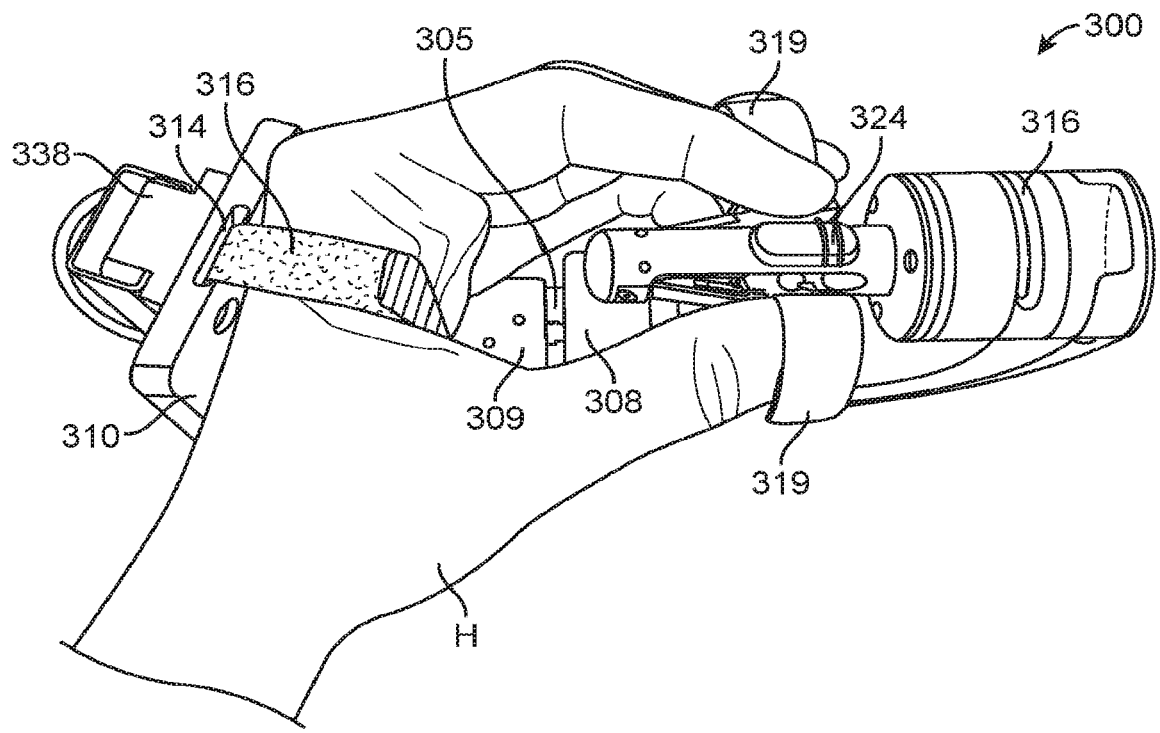
FIG. 5 is a view of the control device of FIG. 4 engaged by a user's hand.

FIG. 4 is a perspective view of a mechanically ungrounded master control device 300 (e.g., an embodiment of the mechanically ungrounded master control device 108). FIG. 5 is a view of the control device 300 engaged by a user's hand H. The control device 300 has a chassis 302, including an arm portion 304 and arm portion 306. The chassis 302 is formed from a rigid material that may include for example, polymer, ceramic, or metal materials. The arm portion 306 is angled (e.g., between 0 and 90 degrees) with respect to the arm portion 304. A raised platform portion 308 extends from the arm portion 304. The arm portion 304 includes a pair of parallel elongated supports 305. The elongated supports 305 extend into and couple the chassis 302 to a slide portion 309. The slide portion 309 may include a single channel into which the elongated supports 305 extend or may include two channels with one for each of the elongated supports. The slide portion 309 is slidably adjustable along the elongated supports 305. During use, the slide portion 309 may be movable and continuously adjustable relative to the supports 305 or may be fixable relative to the supports at discrete extension lengths. A stop bar or other mechanism (not shown) may prevent the slide portion 309 from sliding off and disconnecting from the elongated supports 305. A plate 310 is coupled to one end of the slide portion 309 by a pivot joint 312 that allows the plate to pivot with respect to the chassis 302 and slide portion 309. The pivotable plate 310 includes a slot 314 through which a strap 316 extends. The strap 316 may have a buckle, a Velcro® section, or other fastening mechanism for holding the back of hand H against the plate 310. Thus, the back of hand H is engaged with the plate 310. As shown in FIG. 5, with the hand H engaged with and supported by the plate 310, the hand H is pivotable with the plate 310 relative to the chassis 302. In one aspect, when strap 316 is in place and secured, a presence detection switch may be activated.

A master tool grip portion 314 is rotatably mounted to a housing 316 at an end of the arm portion 306, opposite the platform 308. The tool grip portion 314 includes a shaft 318 which extends into and rotates with respect to the housing 316. Two pivotable finger engagement devices 320 (e.g., levers) are pivotally mounted to shaft 318 at an end of the shaft opposite of the housing 316. Each lever 320 has a contact plate 322 mounted on an end of the lever opposite the end mounted on shaft 318. User S2 typically can grasp the two contact plates 322 between the thumb and middle finger and depress contact plates 322 toward shaft 318 to increase the grasp of the teleoperated slave surgical instrument end effector. Thus, levers 320 are mounted to shaft 318 in a way that emulates the grasping, or other operation, of the tool end effector. Optionally, a single lever 320 may be used. With the contact plates 322 grasped as described, the user S2 may also twist the shaft 318 relative to the housing 316 in a way that emulates the rotation of the tool end effector. Straps 319 are sized to couple the fingers of hand H to the contact plates 322. The strap 319 may have a buckle, a Velcro® section, or other fastening mechanism for holding the fingers to the contact plates 322. A finger grip Cartesian coordinate system ($X_F$, $Y_F$, $Z_F$) may be generally centered in the shaft 318, behind the contact plates 322.

An optional switch 324 is mounted to the top of the shaft 318. The switch 324 may be actuated by the forefinger of hand H. An optional switch 326 is mounted to the bottom of the shaft 318. The switch 326 may be actuated by the ring finger or littlest finger of the user hand H. The switches 324, 326 may be spring loaded buttons, slide mechanisms, or other switching mechanisms known in the art. The switches 324, 326 may be mapped to any of a variety of functions and may be mapped to the same or different functions. Switch functions may include a reset mechanism for moving images of virtual instruments to a default reset position in a displayed image. Alternatively, switch functions may allow selection between a ghost hand shaped indicator. Alternatively, switch functions may enable or disable a telestrator. Alternatively, switch functions may allow switching between medical tools or manipulator arms if the user S2 is controlling instruments 104, rather than virtual instruments. Other functions associated with keypad or foot pedal functions of the surgeon console 106 may be mapped to the switches of the control device 300. Additional switches 324 or 326 may optionally be added.

A sensor 328 may be located in or on the housing 316 to measure the rotation of shaft 318, and thus the rotation of the fingers of the hand H, about the axis $Z_F$, while the base of hand H remains in a generally neutral, unchanged position in the finger grip coordinate system. In one embodiment, the sensor 328 may be a potentiometer.

A sensor 330 is positioned on the chassis 302 or slide portion 309, generally below the elongated supports 305. The sensor 330 tracks position and orientation of the control device 300 in a work space relative to a fixed reference point. A sensor Cartesian coordinate system ($X_S$, $Y_S$, $Z_S$) may be generally centered at the sensor 330. In one embodiment, the sensor 330 may be a six degree of freedom (6 DOF) electromagnetic (EM) sensor. In alternative embodiments, the sensor 330 may be an optical tracking sensor, a fiber optic shape sensor, or another type of sensor known in the art. The sensor 330 may serve to track movements, such as the movements of the user's wrist and forearm, to rotate the tool grip portion 314. For some applications, the preferred reference coordinate system may be the finger grip coordinate system, so any movements measured in the sensor coordinate system may be transformed by an applied transformation from the sensor coordinate system to the finger grip coordinate system. The sensor 330 may be recessed with the chassis 302 and/or slide portion 309 such that the control device 300 has a flat bottom surface that allows the control device to rest stably on a flat surface, which allows the user to easily grasp the device to begin using it.

One or more switches 332 are mounted in the platform 308. The switch 332 may extend from a surface of the platform 308 near the fourth or fifth digit of the user hand H for activation by those fingers. Alternatively, the switch 332 may extend from a surface of the platform 308 near the fifth digit (thumb) for activation thereby. The switches 332 may be spring loaded buttons, slide mechanisms, or other switching mechanisms known in the art. The switches 332 may be mapped to any of a variety of functions such as those described above for switches 324, 326. Mounting the switches 332 on the raised platform 308 provides enhanced ergonomic access to the switches by the fingers. Optionally, one or more switches 332 are on the chassis.

The control device 300 may further include a controller 334 that includes a microprocessor configured for processing one or more signals from the sensors 328, 330, one or more position states of the switches 324, 326, 332 and/or movement of the one or more levers 320. The processed signal(s) and/or position state(s) may be transmitted through a wireless adapter 336 for receipt by, for example, controller 110. The wireless adapter may use wireless communication protocols such as Bluetooth, IrDA, HomeRF, IEEE 802.11, DECT, and Wireless Telemetry. Data may be transmitted, for example, at a rate of approximately 60 Hz for proctoring applications and at a rate of approximately 1 kHz or higher for instrument control applications. Other transmission rates may optionally be used. The controller 334 and/or adaptor 336 may be powered by a power source 338, such as a battery. With a wireless adapter 336 and a wireless power source 338, the control device 300 may be untethered. That is, all power and data transmission may be provided without a physical tethering of the control device to another part of the medical system 100. In alternative embodiments, a tethered (e.g., corded) coupling may couple control device 300, including processors, sensors, or signal transmitters, to power supplies, processors, and/or signal receivers with the teleoperated medical system. Further, in a tethered embodiment, an optical fiber shape sensor may extend through the tether to provide position and orientation tracking of the control device 300. Placing a battery 338 or other type of weight behind the plate 310 and thus behind the user's hand H may provide a counter balance to the grip 314 and housing 316.

In use, the hand H of the user S2 may be fastened to the control device 300. As the user S2 moves his fingers to manipulate the grip 314, actuate the switches 324, 326, 332, or move the levers 320, the motion is recorded and sent to the controller 110 to, for example, generate movement of virtual instrument images on a display for proctoring the user S1 or to generate movement of the instruments 104 in the surgical environment.

Figure 6:
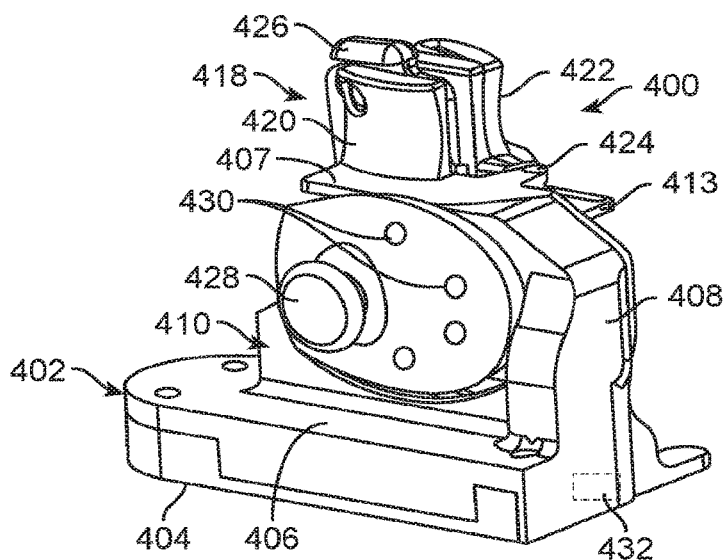
FIG. 6 is a perspective view of a mechanically ungrounded master control device according to another embodiment.
Figure 7:
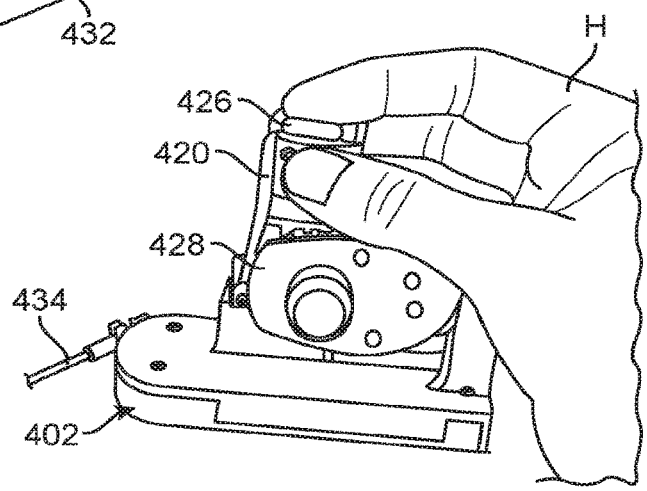
FIGS. 7 and 8 are views of the control device of FIG. 6 engaged by a user's hand.
Figure 8:
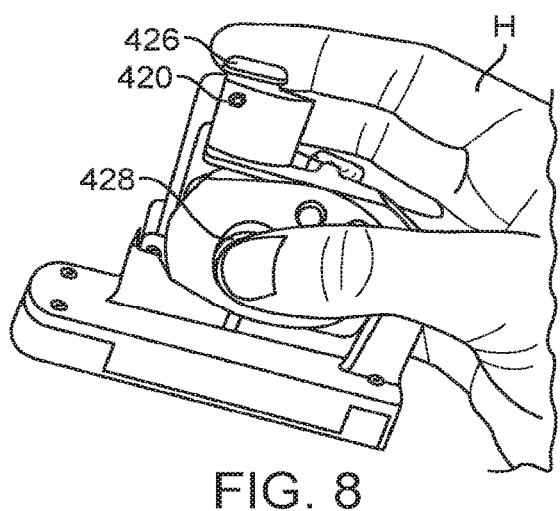
Figure 9:
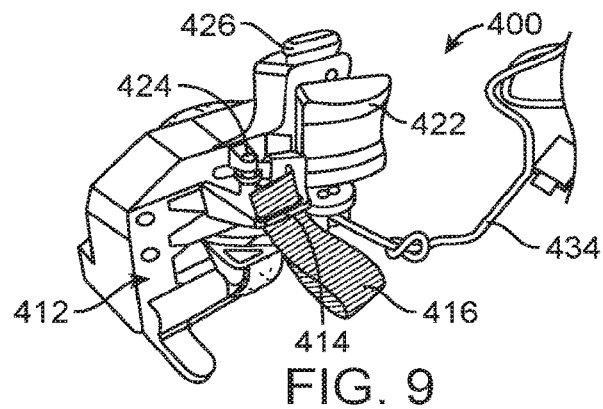
FIG. 9 is another perspective view of the control device of FIG. 6.

FIG. 6 is a perspective view of a mechanically ungrounded master control device 400 (e.g., an embodiment of the mechanically ungrounded master control device 108). FIGS. 7 and 8 show the control device 400 engaged with a user hand H (e.g. the hand of user S2). The control device 300 has a chassis 402 having a flat bottom surface 404 for resting stably on a flat surface to allow easy grasping when the user first picks up the device, a platform 406 for supporting a thumb of hand H in a resting position, a platform 407 for supporting a thumb of hand H in a gripping position, and a body portion 408 sized to fit comfortably with a palm of hand H. The chassis 402 may have a side 410 accessible primarily by a user's thumb and a side 412 accessible primarily by the user's second through fourth digits. The chassis 402 is formed from a rigid material that may include for example, polymer, ceramic, or metal materials. The chassis side 412 includes a slot 414 through which a strap 416 extends. The strap 416 may have a buckle, a Velcro® section, or other fastening mechanism for holding the palm of hand H to the side 412 of the chassis 402. Side 412 may include one or more finger rests 413 for supporting one or more of the fingers of hand H. As thus engaged, the palm of hand H is engaged with and supported by the chassis 402.

A tool grip portion 418 extends from the top of the chassis 402 and includes a finger engagement member 420 and a finger engagement member 422. In this embodiment, the engagement member 420 is rigidly coupled or integrally formed with the chassis platform 407 and the engagement member 422 is pivotally coupled by a joint 424 to the engagement member 420 and chassis platform 407. In this configuration, engagement member 422 is a pivotable finger engagement device and moves relative to the chassis 402, but engagement member 420 does not move relative to the chassis. In alternative embodiments, the engagement members 420, 422 may be pivotally coupled such that both engagement members are movable relative to the chassis 402. User S2 typically can grasp the two engagement members 420, 422 between the thumb and middle finger (i.e., thumb on member 420 and third digit on member 422) and depress engagement member 422 toward engagement member 420 to increase the grasp of the teleoperated slave surgical instrument end effector. Thus, engagement members 420, 422 are mounted in a way that emulates the grasping, or other operation, of the tool end effector jaw or jaws.

A switch 426 extends between the engagement members 420, 422. The switch 426 may be actuated by the forefinger of hand H. The switch 426 may be a spring loaded button, a slide mechanism, or other switching mechanisms known in the art. The switch 426 may be mapped to any of a variety of different functions. Switch functions may include a reset mechanism for moving images of virtual instruments to a default reset position in a displayed image. Alternatively, switch functions may allow selection between a hand-shaped indicator or other pointer as described above. Alternatively, switch functions may enable or disable a telestrator. Alternatively, switch functions may allow switching between medical tools or manipulator arms if the user S2 is controlling instruments 104, rather than virtual instruments. Other functions associated with keypad or foot pedal functions of the surgeon console 106 (e.g., electrosurgical energy application, electrosurgical energy level control, suction/irrigation control, focus control, zoom control, etc.) may be mapped to the switches of the control device 400.

An continuous motion input controller 428, such as a joy stick toggle ever may be coupled to the side 410 of the chassis 402 for operation by the thumb of hand H. The joystick 428 may be used, for example, to dictate the state of a ghost tool, to select from among different ghost tools in a virtual image, or to toggle a virtual image of ghost tools on or off. Alternatively the joystick may be used to operate any of the switch functions described above. One or more switches 430 may be accessible by the thumb on the side 410 of the chassis 402. Any of the previously described switch or joystick functions may be mapped to these switches 430.

A sensor 432 is positioned in the chassis 302. The sensor 432 may track position and orientation of the control device 400 in a work space relative to a fixed reference point. In one embodiment, the sensor 330 may be a wireless 6 DOF electromagnetic (EM) sensor. In alternative embodiments, the sensor 330 may be an optical tracking sensor, a potentiometer, a fiber optic shape sensor, or another type of sensor known in the art. In alternative embodiments, a wired EM sensor may send a sensor signal via a tether 434 from the control device 400 to a controller 110.

The control device 400 may further include a controller (not shown) including a microprocessor for processing signals from the sensor 432, position states of the switches 426, 430 and/or movement of the engagement member 422. The processed signals and/or position states may be transmitted through a wireless adapter (not shown) for receipt by, for example, controller 110. The wireless adapter may use wireless communication protocols such as Bluetooth, IrDA, HomeRF, IEEE 802.11, DECT, and Wireless Telemetry. The controller and/or adaptor may be powered by a power source, such as a battery. With a wireless adapter and a wireless power source, the control device 400 may be untethered. That is, all power and data transmission may be provided without tethering the control device to another part of the medical system 100. In alternative embodiments, a tethered or corded coupling may couple control device 400, including processors, sensors, or signal transmitters, to power supplies, processors, and/or signal receivers with the teleoperated medical system.

In use, the hand H of the user S2 may be fastened to the control device 400 via the strap 416. As the user S2 moves his fingers to manipulate the grip 418, actuate the switches 326, 430, or move the joystick 428, the motion is sensed and sent to the controller 110 to, for example, generate movement of virtual instrument images on a display for proctoring the user S1 or to generate movement of the instruments 104 in the surgical environment.

Figure 10:
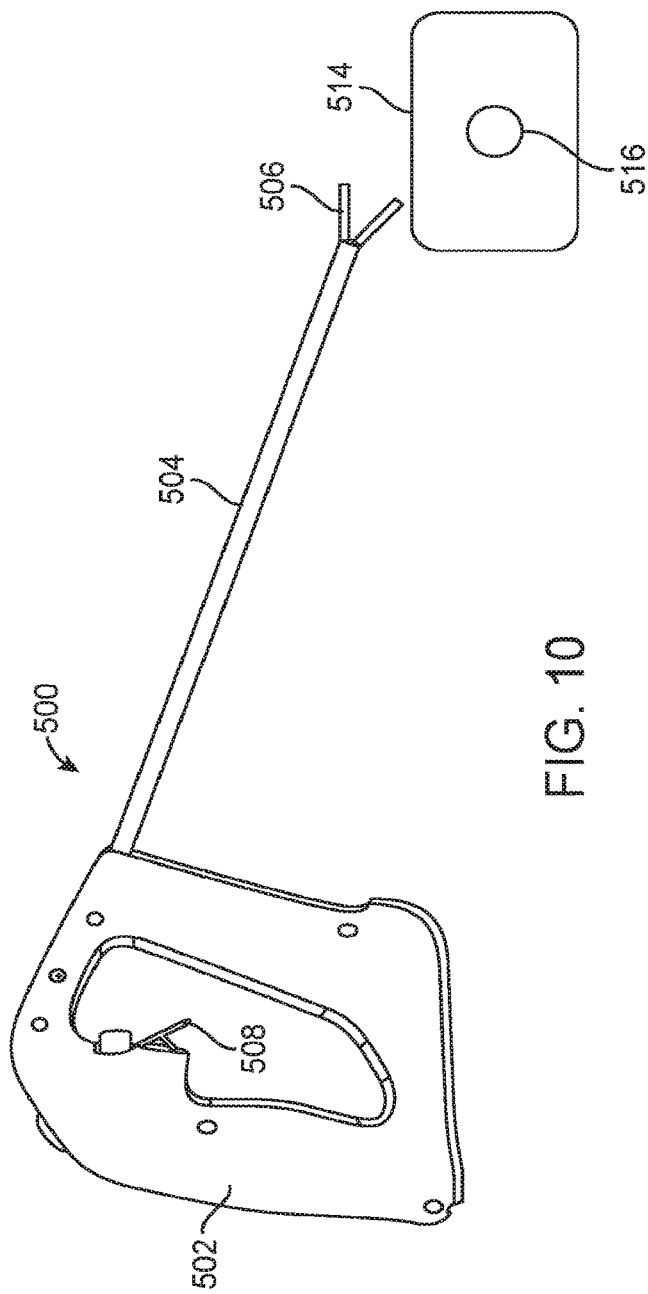
FIG. 10 is a side view of a mechanically ungrounded master control device according to another embodiment.
Figure 11:
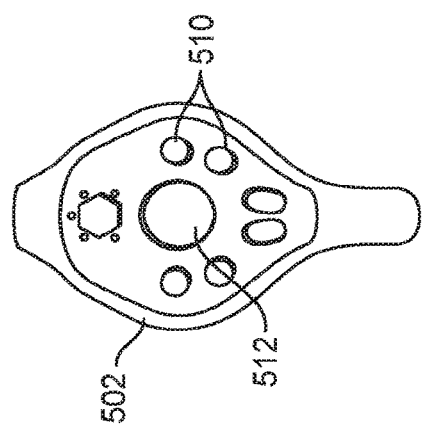
FIG. 11 is a side view of the handle of the control device of FIG. 10.

FIG. 10 is a side view of a mechanically ungrounded master control device 500 according to another embodiment. FIG. 11 is a side view of a handle 502 of the control device 500. In this embodiment, the control device is configured to control a hand-held, minimally invasive instrument (e.g., a laparoscopic instrument) or virtual image of such an instrument for use in a proctoring situation. In various other embodiments, the instrument 500 may be a uterine manipulator, a suction irrigator, a stapler, or other elongated instrument. The handle 502 may be coupled to an elongated shaft 504 with a distal end effector 506. Alternatively, the shaft and end effector components may be omitted in a proctoring configuration. The control device 500 includes a trigger 508, a joystick lever 512, and a variety of switches 510 on the handle 502 which may be mapped as described in the embodiments above. For example, switch functions may include a reset mechanism for moving images of virtual instruments to a default centered reset position in a displayed image. Alternatively, switch functions may allow selection between a ghost hand shaped indicator. Alternatively, switch functions may enable or disable a telestrator. Alternatively, switch functions may allow switching between medical tools or manipulator arms if the user S2 is controlling instruments 104, rather than virtual instruments. Other functions associated with keypad or foot pedal functions of the surgeon console 106 may be mapped to the switches of the control device 500. The handle 502 may also include a variety of sensors for tracking position and/or orientation of the handle. In use, the hand H of the user S2 may grab the handle 502. As the user S2 moves his fingers to manipulate the trigger 508, actuate the switche(s) 510, or move the joystick 512, the motion is recorded and sent to the controller 110 to, for example, generate movement of virtual instrument images on a display for proctoring the user S1 or to generate movement of a slave laparoscopic instrument in the surgical environment. In some embodiments, the control device 500 may be used together with an anatomic model 514 (e.g., a model of a human abdomen) having holes 516 to simulate port positions in a patient abdomen. This allows the surgeon or proctor to experience forces and limitations similar to those that would be experienced if the instrument 500 was docked with an actual patient.

One or more elements in embodiments of the invention may be implemented in software to execute on a processor of a computer system such as a control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disc, a hard disc, or other storage device, the code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A teleoperated medical system comprising:
a mechanically ungrounded master control device including:
a rigid chassis engageable with one or more fingers of a user's hand,
at least one pivotable finger engagement device operative to control at least one of: movement of a virtual tool or a physical tool end effector,
at least one sensor of a position and an orientation of the rigid chassis in a surgical environment, a switch coupled to the rigid chassis and manipulatable by a second finger of the user's hand while a first finger of the user's hand is engaged with the at least one pivotable finger engagement device, and a plate pivotally coupled to the rigid chassis and configured to contact a backside of the user's hand, the plate being pivotable about a rotational axis of the plate with reference to the rigid chassis;

a console including:

a mechanically grounded master control device operative to control at least one of: movement of the virtual tool or movement of the physical tool end effector, and a display operative to display at least one of the virtual tool or the physical tool end effector; and a manipulator operative to manipulate the physical tool end effector in response to at least one of: movement of the mechanically grounded master control device or movement of the mechanically ungrounded master control device.

2. The teleoperated medical system of claim 1, wherein the mechanically ungrounded master control device further comprises at least one sensor of a rotational motion of the at least one pivotable finger engagement device about a longitudinal axis of the rigid chassis.

3. The teleoperated medical system of claim 1, wherein the mechanically ungrounded master control device further comprises a slide portion slidably engaged with the rigid chassis, the slide portion pivotally coupled to the plate.

4. The teleoperated medical system of claim 1, wherein the at least one sensor includes a six degree of freedom electromagnetic sensor.

5. The teleoperated medical system of claim 1, further comprising a processor coupled to the rigid chassis of the mechanically ungrounded master control device.

6. The teleoperated medical system of claim 1, wherein the at least one pivotable finger engagement device includes two pivotable finger engagement devices coupled to a shaft that is rotatably coupled to the rigid chassis.

7. The teleoperated medical system of claim 6, wherein the switch is positioned between the two pivotable finger engagement devices.

8. The teleoperated medical system of claim 1, wherein the at least one pivotable finger engagement device is a single pivotable finger engagement device pivotally coupled to the rigid chassis.

9. The teleoperated medical system of claim 1, wherein the mechanically ungrounded master control device further comprises a shaft having a first end and a second end, the shaft rotatably coupled to the rigid chassis at the first end of the shaft, the shaft being rotatable about a longitudinal axis with reference to the rigid chassis, wherein the plate is positioned closer to the second end of the shaft than to the first end of the shaft.

10. The teleoperated medical system of claim 9, wherein the rotational axis of the plate is nonparallel to the longitudinal axis.

11. The teleoperated medical system of claim 1, wherein the mechanically ungrounded master control device is operative to control the movement of the virtual tool and the mechanically grounded master control device is operative to control the movement of the physical tool end effector.

12. The teleoperated medical system of claim 1, wherein the mechanically ungrounded master control device is operative to control the movement of the virtual tool and the display is operative to display the virtual tool and the physical tool end effector.

13. The teleoperated medical system of claim 1, wherein the mechanically ungrounded master control device is a first mechanically ungrounded master control device and the virtual tool is a first virtual tool, and further comprising:

a second mechanically ungrounded master control device operative to control movement of a second virtual tool, wherein the display is further operative to display the second virtual tool.

14. The teleoperated medical system of claim 1, wherein the physical tool end effector is a first physical tool end effector, and further comprising a second physical tool end effector, wherein the mechanically grounded master control device is operative to control the movement of the first physical tool end effector and the mechanically ungrounded master control device is operative to control movement of the second physical tool end effector.

15. A mechanically ungrounded master control device comprising:

a rigid chassis comprising a body portion and an extended portion coupled to the body portion;

a first finger engagement device and a second finger engagement device, the first finger engagement device coupled to the extended portion of the rigid chassis and configured to engage with a thumb of a hand of a user operating the mechanically ungrounded master control device, the second finger engagement device coupled to the extended portion of the rigid chassis and configured to engage with a middle finger of the hand of the user operating the mechanically ungrounded master control device, at least one of the first finger engagement device or the second finger engagement device pivotally coupled to the rigid chassis and configured to pivot about an associated pivot axis with reference to the rigid chassis, and the extended portion of the rigid chassis extending parallel to the pivot axis associated with the first finger engagement device or the second finger engagement device;

a sensor of a position and an orientation of the rigid chassis in a physical environment;

a first input device coupled to the rigid chassis between the first finger engagement device and the second finger engagement device, the first input device manipulatable by an index finger of the hand of the user operating the mechanically ungrounded master control device while the thumb is engaged with the first finger engagement device and the middle finger is engaged with the second finger engagement device; and a second input device coupled to the rigid chassis, the second input device manipulatable by the thumb of the hand of the user operating the mechanically ungrounded master control device when the thumb is not engaged with the first finger engagement device.

16. The mechanically ungrounded master control device of claim 15, wherein:

the first finger engagement device is fixed with respect to the rigid chassis;

the second finger engagement device is pivotally coupled to the rigid chassis; and the second finger engagement device is moveable toward or away from the first finger engagement device in a grasping motion of the middle finger and the thumb of the hand of the user operating the mechanically ungrounded master control device.

17. The mechanically ungrounded master control device of claim 15, wherein:
the first finger engagement device and the second finger engagement device are pivotally coupled to the rigid chassis and are pivotable with respect to each other in a grasping motion of the thumb and the middle finger of the hand of the user operating the mechanically ungrounded master control device.

18. The mechanically ungrounded master control device of claim 15, further comprising:
a first platform coupled to a first side of the rigid chassis, the first platform configured to support the thumb of the hand of the user operating the mechanically ungrounded master control device in a gripping position when the thumb is engaged with the first finger engagement device; and
a second platform coupled to the extended portion of the rigid chassis on the first side of the rigid chassis, the second platform configured to support the thumb of the hand of the user operating the mechanically ungrounded master control device in a resting position away from the first finger engagement device.

19. The mechanically ungrounded master control device of claim 18, further comprising a third platform coupled to a second side of the rigid chassis, the third platform configured to support one or more fingers of the hand of the user operating the mechanically ungrounded master control device.

20. The mechanically ungrounded master control device of claim 15, wherein:
the body portion of the rigid chassis comprises a flat bottom on which the mechanically ungrounded master control device rests stably on a flat surface.

21. The mechanically ungrounded master control device of claim 15, wherein the first input device is a switch positioned between the first and second finger engagement devices.

22. The mechanically ungrounded master control device of claim 15, wherein the second input device includes a joystick coupled to the rigid chassis.

* * * * *